United States Patent [19]

Kase et al.

[11] Patent Number: 4,847,435

[45] Date of Patent: Jul. 11, 1989

[54] PROCESS FOR THE RECOVERY OF HIGH-PURITY M-ETHYLPHENOL

[75] Inventors: Keizo Kase, Ichihara; Tsutomu Idai, Noda; Kazumasa Ishii, Ichihara; Eiji Takahashi, Chiba, all of Japan

[73] Assignee: Maruzen Petrochemical Co., Ltd., Tokyo, Japan

[21] Appl. No.: 206,227

[22] Filed: Jun. 13, 1988

[30] Foreign Application Priority Data

Jun. 24, 1987 [JP] Japan ................................ 62-156987

[51] Int. Cl.$^4$ ............................................. C07C 37/50
[52] U.S. Cl. ...................................... 568/750; 568/805
[58] Field of Search ................ 568/749, 750, 751, 805

[56] References Cited

U.S. PATENT DOCUMENTS

| | | |
|---|---|---|
| 3,702,886 | 11/1972 | Argauer et al. |
| 3,709,979 | 1/1973 | Chu. |
| 3,832,444 | 8/1974 | Rosinski et al. ................ 423/328 |
| 4,016,245 | 4/1977 | Plank et al. ................... 423/328 |
| 4,032,581 | 6/1977 | Tasaka et al. .................. 568/750 |
| 4,046,859 | 9/1977 | Plank et al. ................... 423/328 |
| 4,532,368 | 7/1985 | Swanson et al. ................ 568/791 |
| 4,769,499 | 9/1988 | Miwa et al. .................... 568/758 |

FOREIGN PATENT DOCUMENTS

| | | | |
|---|---|---|---|
| 44-53 | 1/1969 | Japan | 568/791 |
| 0046729 | 4/1979 | Japan | 568/750 |
| 0046730 | 4/1979 | Japan | 568/750 |

OTHER PUBLICATIONS

The Journal of Catalysis, 67, 218–222, (1981), Catalysis by Crystalline Aluminosilicates: Characterization of Intermediate Pore-Size Zeolites by the "Constraint Index".

*Primary Examiner*—Werren B. Lone
*Attorney, Agent, or Firm*—Frishauf, Holtz, Goodman & Woodward

[57] ABSTRACT

A meritorious, commercially successful process for the recovery of a high-purity m-ethylphenol from ethylphenol mixtures containing m- and p-ethylphenols as the major components is disclosed. As it is well known in the art, the ethylphenol mixtures containing m- and p-ethylphenols as the major components can easily be prepared by ethylation of phenol with ethylene or ethanol by a simple operation. Accordingly, a process for the recovery of high-purity m-ethylphenol from ethylphenol mixtures containing m- and p-ethylphenols as the major components can give great influences in the commercial production of high-purity m-ethylphenol. m-Ethylphenol is a useful intermediate for the production of pharmaceuticals and agricultural chemicals. The process comprises simply contacting an ethylphenol mixture containing m- and p-ethylphenols as the major components with a specific crystalline aluminosilicate catalyst under heating.

24 Claims, No Drawings

PROCESS FOR THE RECOVERY OF HIGH-PURITY M-ETHYLPHENOL

BACKGROUND OF THE INVENTION

1. Field of the Invention

The present invention relates to a process for the recovery of m-ethylphenol, and more particularly, relates to a process for the recovery of high-purity m-ethylphenol by contacting a mixture of ethylphenols containing m- and p-ethylphenols with a specific catalyst under heating, thereby selectively dealkylating p-ethylphenol to phenol and ethylene.

m-Ethylphenol is useful as an intermediate for the production of pharmaceuticals and agricultural chemicals. Since pharmaceuticals and agricultural chemicals are related directly or indirectly to human lives, the presence of impurities in the products is not permissible. Thus, raw materials and intermediates with a purity as high as possible are desired for the production of pharmaceuticals and agricultural chemicals, and therefore, high-purity m-ethylphenol is required when it is used as an intermediate for the production of pharmaceuticals and agricultural chemicals.

2. Description of the Prior Art

The conventional process for the preparation of m-ethylphenol comprises sulfonation of ethylbenzene, hydrolysis of the thus produced ethylbenzenesulfonic acid mixture excepting the m-isomer, and alkali fusion of the remaining m-ethylbenzenesulfonic acid. This process has long been practiced industrially.

It is also known that a mixture of ethylphenol isomers is obtained by alkylation of phenol with ethylene, ethanol, etc. (Japanese Patent Publication No. Sho 44(1969)-53; U.S. Pat. No. 4,532,368). However, among the ethylphenols, m-ethylphenol and p-ethylphenol have very close boiling points, and it is practically impossible to isolate m-ethylphenol from a mixture of ethylphenols by distillation. No industrial process has been known which allows purification of m-ethylphenol from ethylated products of phenol.

Development of a new process of preparation of m-ethylphenol has been desired because the conventional process of its preparation from ethylbenzene via ethylbenzenesulfonic acid has many problems such as tedious multi-step operation, inferior operational surroundings associated with handling of dangerous high-temperature sulfuric acid and sodium hydroxide, corrosion of equipment caused by the use of sulfuric acid, and disposal of waste water containing sulfuric acid and alkali.

On the other hand, the ethylation of phenol is advantageous for the preparation of an ethylphenol mixture because it requires fewer steps and simpler operation. This process, however, does not permit selective preparation of high-purity m-ethylphenol because it is difficult to separate m-ethylphenol and p-ethylphenol contained in the product mixture.

SUMMARY OF THE INVENTION

The present invention aims at solving the above-described problems associated with the conventional processes.

Thus, the object of the present invention is to provide a process which permits facile, high-yield, and economical recovery of high-purity m-ethylphenol from an ethylphenol mixture containing m-ethylphenol and p-ethylphenol.

We have made intensive studies toward realizing the above-described object, and succeeded in completing the present invention by the finding that high-purity m-ethylphenol can be recovered from a mixture of m-ethylphenol and p-ethylphenol by the use of a specific crystalline aluminosilicate catalyst which selectively dealkylates p-ethylphenol only.

Thus, the present invention relates to a process for the recovery of high-purity m-ethylphenol characterized in that p-ethylphenol is selectively dealkylated by allowing to contact a mixture of ethylphenols containing m- and p-ethylphenols under heating with (i) a crystalline aluminosilicate catalyst which is obtained by calcining a crystalline aluminosilicate with a constraint index of 1-15, after it is incorproated with one or more compounds containing phosphorus and one or more compounds containing the element selected from the group consisting of manganese, cobalt, silicon and the Group IIA elements of the Periodic Table, or incorporated with one or more compounds containing silicon or phosphorus, or (ii) a crystalline aluminosilicate catalyst which is obtained by incorporating one or more compounds containing silicon to a crystalline aluminosilicate with a constraint index of 1-15, without subjecting to calcination.

The catalyst used in the present invention is (i) a crystalline aluminosilicate catalyst which is obtained by calcining a crystalline aluminosilicate with a constraint index of 1-15, after it is incorporated with one or more compounds containing phosphorus and one or more compounds containing the element selected from the group consisting of manganese, cobalt, silicon and the Group IIA elements of the Periodic Table, or incorporated with one or more compounds containing silicon or phosphorus, or (ii) a crystalline aluminosilicate catalyst which is obtained by incorporating one or more compounds containing silicon to a crystalline aluminosilicate with a constraint index of 1-15, without subjecting to calcination. The term "constraint index" as used here is an index value as defined in Journal of Catalysis, 67, 218 (1981), and is represented by the ratio of cracking rates of n-hexane and 3-methylpentane during a competitive cracking reaction thereof. More specifically, an equimolar vapor mixture of n-hexane and 3-methylpentane, after diluted with five times volume of helium, is allowed to flow through a catalyst for 20 min with an LHSV of 1 hr$^{-1}$, and the proportions of n-hexane and 3-methylpentane remained in the product mixture are determined. The constraint index is defined by the equation described below:

$$\text{Constraint index} = \frac{\log (\text{fraction of n-hexane remaining})}{\log (\text{fraction of 3-methylpentane remaining})}$$

Incidentally, the competitive cracking reaction of n-hexane and 3-methylpentane to determine the constraint index shown above is conducted at the temperature within the range of 287°–510° C., and the temperature is so determined that the overall conversion rate is within 10–60%. With low-activity catalysts which do not allow the conversion rate to exceed 10% at a temperature below 510° C., the LHSV is lowered to raise the conversion rate to the range of 10–60%. Relative sizes of the pores in crystalline aluminosilicates can be determined by measurements of the constraint index by the use of the aluminosilicate catalysts. That is, n-hexane has a relatively smaller molecular diameter than 3-methylpentane, and therefore, those crystalline aluminosilicates with a pore size which allows penetration of n-hexane but does not permit penetration of 3-methylpentane, show constraint indexes larger than 30. On the other hand, those crystalline aluminosilicates with a larger pore size which permits a relatively free penetration of both n-hexane and 3-methylpentane, show values smaller than 1 due to the inherent cracking reactivities of n-hexane and 3-methylpentane. An example of the former case is erionite which has an eight-membered ring at the entrance to the pore, and examples of the latter case are rare-earth element containing Y-type zeolite (REY) and H-type mordenite which have a twelve-membered ring at the entrance to the pore.

The crystalline aluminosilicates used in the present invention with the constraint index (hereinafter abbreviated occasionally as CI) of 1–15 are zeolites with a silica/alumina ratio of not less than 20 and with a medium-size pore, and thus the degree of the ease of the penetration of p-ethylphenol and m-ethylphenol into the pore can be regulated by the difference of the molecular sizes of them. It is known that examples which satisfy the above requirements are ZSM-5 (CI 8.3) (U.S. Pat. No. 3,702,886) and ZSM-11 (CI 8.7) (U.S. Pat. No. 3,709,979), ZSM-12 (CI 2.0) (U.S. Pat. No. 3,832,449), ZSM-35 (CI 4.5) (U.S. Pat. No. 4,016,245), and ZSM-38 (CI 2.0) (U.S. Pat. No. 4,046,859), developed by Mobil Oil Corp. Preferred crystalline aluminosilicates used in the present invention are pentasil-type zeolites, such as ZSM-5, ZSM-11 and the like.

the crystalline aluminosilicates described above have crystal diameters of 0.05–10 μm, and preferably 0.2–3 μm. The crystalline aluminosilicates mentioned above contain exchangeable cations near the aluminum atoms to neutralize the electric charge. When preparing the catalysts used in the present invention, the cations are firstly replaced with $H^+$, $NH_4^+$, or polyvalent cations. The crystalline aluminosilicates may be used in the powder form or after molding. They may be molded from crystalline aluminosilicates themselves or by admixture with suitable binders. Examples of such binders are clays, diatomaceuous earths, silica, alumina, and metal oxides. The contents of such binders in the whole catalysts should be below 90 wt% and preferably between 2–50 wt%. In order to prepare the crystalline aluminosilicate catalysts used in the present invention, the said crystalline aluminosilicate is allowed to contact by a suitable manner with one or more compounds containing phosphorus and one or more compounds containing the element selected from the group consisting of manganese, cobalt, silicon and Group IIA elements of the Periodic Table, or to contact one or more compounds containing silicon or phosphorus. In general, no restriction exists as to the mode of the contact. For example, they may be prepared by drying and calcining the said crystalline aluminosilicate after immersion in a solution of compounds containing the said elements, and removal of the solvent by filtration or evaporation. Alternatively, they may be prepared by drying a calcining the crystalline aluminosilicate after making contact with compounds containing the said elements in the vapor phase with an inert gas such as nitrogen, helium, argon, carbon dioxide, and steam.

In the cases where one or more compounds containing manganese, cobalt or Group IIA elements are used in combinaton with one or more compounds containing phsophorus, the order of contact of these compounds with the crystalline aluminosilicate is not restricted. However, when one or more compounds containing silicon are used in combination with one or more compounds containing phosphorus, it seems like preferable to contact the phosphorus containing compound or compounds, firstly, with the crystalline aluminosilicates. Further, it is to be noted that when the crystalline aluminosilicate catalyst is prepared by incorporating one or more compounds containing silicon to a crystalline aluminosilicate, a calcination treatment is not necessarily required. That is, it is sufficient that if a crystalline aluminosilicate is impregnated with one or more compounds containing silicon, and dried.

The Group IIA elements of the Periodic Table as referred in the present invention are beryllium, magnesium, calcium, strontium, barium, and radium, and preferably magnesium, calcium, strontium, and barium. In the present invention, any solvent may be used to dissolve the compounds containing the said elements as far as they are inert to the compounds and to the crystalline aluminosilicates. Examples of suitable solvents are water, inorganic acids such as hydrochloric acid, nitric acid and sulfuric acid, aromatic hydrocarbons such as benzene, toluene, xylene and ethylbenzene, aliphatic hydrocarbons such as hexane, heptane, octane, nonane and decane, cycloaliphatic hydrocarbons such as cyclohexane, methylcyclohexane and ethylcyclohexane, alcohols such as methanol, ethanol, propanol and butanol, carboxylic acids such as formic acid, acetic acid and propionic acid, halogenated hydrocarbns such as dichloromethane, chloroform, carbon tetrachloride, dichloroethane and trichloroethane, ketones such as acetone, methyl ethyl ketone, pentanone, hexanone and methyl isobutyl ketone, ethers such as diethyl ether, diisopropyl ether, dibutyl ether, tetrahydrofuran and dioxane, carboxylates such as methyl formate, ethyl formate, propyl formate, butyl formate, methyl acetate, ethyl acetate, propyl acetate, butyl acetate, methyl butyrate and ethyl butyrate. Generally, the most useful solvent is water. Examples of phosphorus containing compounds are ammonium phosphate, diammonium hydrogenphosphate, ammonium dihydrogenphosphate, diphenylphosphine chloride, trimethyl phosphite, phosphorus trichloride, phosphoric acid, phenylphosphonic dichloride, trimethyl phosphate, diphenyl phosphite, diphenylphosphinic acid, acidic methyl phosphate, and other acidic esters of phosphoric acid. Examples of compounds containing manganese, cobalt, magnesium, calcium, strontium, and barium used in combination with the phosphorus containing compound or compounds are carboxylates (such as acetates, oxalates, lactates, tartrates, and citrates), carbonates, sulfates, nitrates, and halides. Among them, acetates and nitrates are preferred. As examples of silicon containing compounds, silanes and silicones may be cited. As silanes, alkoxysilanes shown by the general formula (1) are used.

 (1)

(In formula (1), n=0–3, OR represents an alkoxyl group with 1 to 6 carbon atoms, and R' represents an alkyl or an aryl group with 1 to 6 carbon atoms.) Among them, compounds where OR is a methoxyl or an ethoxyl group are preferred, and tetramethoxysilane and tetraethoxysilane where n=0 are particularly preferred.

Silicone oils and silicone greases may be cited as examples of silicone compounds.

In the present invention, the drying of the catalyst is performed at 80°–150° C. for 1–20 hr, and calcination is performed for 1–20 hr at 450°–800° C. in the presence of oxygen such as in the air. The amount of compounds containing phosphorus, manganese, cobalt, silicon, and Group IIA elements of the Periodic Table, which is incorporated into the said crystalline alumninosilicate, is 0.2–40 wt%, and preferably 0.4–25 wt% calculated as the elements based on the crystalline aluminosilicate.

The present invention is performed by allowing the said catalyst to contact with an ethylphenol mixture containing m-ethylphenol and p-ethylphenol, thereby selectively dealkylating p-ethylphenol.

The ethylphenol mixture containing m-ethylphenol and p-ethylphenol which is used in the present invention may also contain phenol, o-ethylphenol, diethylphenol, phenetole, etc. in addition to m- and p-ethylphenols. The molar ratio of m-ethylphenol/p-ethylphenol in the ethylphenol mixture containing m- and p-ethylphenols may vary without specific limitation, but the recovery yield and purity of m-ethylphenol thus obtained will rise as the ratio becomes higher. In general, the mixture containing m- and p-ethylphenol as the major components which is easily obtainable, for example, by distillation of reaction products obtainable by ethylation of phenol with ethylene or ethanol, has m-ethylphenol/p-ethylphenol molar ratio of 0.5–20, and for the reasons stated above, such a mixture containing m- and p-ethylphenol as the major components can suitably be used as the raw material of the process of this invention. The ethylphenol mixture containing m- and p-ethylphenols may be allowed to react by dilution with water (steam), aliphatic hydrocarbons such as hexane, heptane, octane, nonane and decane, aromatic hydrocarbons such as benzene, toluene, xylene and ethylbenzene, nitrogen, helium, or carbon dioxide. The preferred diluent is water (steam). These diluents may be admixed with the ethylphenol mixture containing m- and p-ethylphenols prior to introduction to the reactor, or may be introduced separately into the reactor. The reaction may be performed by a batch process or flow process through a fixed bed or a fluidized bed, but a fixed-bed flow process is particularly preferred. The reaction temperature in the range of 350°–550° C. is preferred, and 400°–500° C. is more preferred because the reaction proceeds too slowly below 300° C. and a temperature above 600° C. tends to shorten the catalyst life by deposition of carbonaceous substances on the catalyst surface. The reaction may be performed either in the vapor phase or in the liquid phase, but the vapor phase is preferred. The reaction pressure is not restricted but is preferably below 50 Kg/cm$^2$, and more preferably below 10 Kg/cm$^2$. When the reaction is performed by a flow system through a fixed bed by the use of molded catalyst, the weight hourly space velocity (WHSV) is 0.05–100 hr$^{-1}$, preferably 0.5–50 hr$^{-1}$, and more preferably 1–30 hr$^{-1}$ based on the catalyst.

In accordance with the process of the present invention under the conditions described above, when an ethylphenol mixture containing m- and p-ethylphenols is allowed to contact with the said catalyst at 350°–550° C., p-ethylphenol diffuses into the pore and decomposes by dealkylation to form ethylene and phenol. On the other hand, since m-ethylphenol has a larger molecular diameter than p-ethylphenol, it practically does not react due to a very slow diffusion rate into the catalyst pore. After selective decomposition of p-ethylphenol in this way, the reaction products are subjected to distillation step either after condensation to a liquid phase or as a vapor phase, and ethylene, phenol, and a small amount of by-products formed by the decomposition, and the diluent described above, when it is used, are removed to recover the desired m-ethylphenol of high purity.

The present invention relates to a process for the recovery of m-ethylphenol from a mixture of m- and p-ethylphenols prepared by ethylation of phenol, which requires fewer reaction steps and simpler operation than the conventional process by an alkali fusion of m-ethylbenzenesulfonic acid. The process of this invention simply comprises selectively decomposing only p-ethylphenol by the use of a specific catalysts. By the process of the present invention, high-purity m-ethylphenol, suitable as an intermediate for pharmaceuticals and agricultural chemicals, may be recovered readily in high yield and economically.

DESCRIPTION OF THE PREFERRED EMBODIMENT

The present invention will be illustrated more specifically by the following Examples, but the present invention is not limited by the Examples.

Example 1

This Example illustrates the preparation of H-ZSM-5/Al$_2$O$_3$, and further illustrates the production of an ethylphenol mixture of m- and p-ethylphenols for use as the raw material of the process of this invention. Accordingly, this Example is not within the scope of this invention, and is given for reference purpose only.

Na-ZSM-5 with a silica/alumina molar ratio of 100 was prepared according to U.S. Pat. No. 3,702,886. The Na-ZSM-5 thus obtained had a silica/alumina molar ratio of 96 as determined by X-ray fluorescence analysis, and had an average crystalline diameter of 1.0 μm as determined by electron microscope. This Na-ZSM-5 (140 g) was soaked in 1,000 ml of 1N aqueous ammonium nitrate, refluxed for 12 hr and kept as it stands, and then the supernatant solution was removed by decantation. The addition of 1,000 ml of 1N aqueous ammonium nitrate, reflux, and decantation described above were repeated three more times, and the solid was washed with water and dried overnight at 120° C. to produce NH$_4$-ZSM-5.

To this NH$_4$-ZSM-5 was added an alumnina sol (Cataloid-AP, produced by Catalysts & Chemicals Ind. Co., Ltd.) in quantity that 10 wt% of the alumina binder is incorporated, and the mixture was mixed thoroughly with water, molded, air-dried overnight at an ambient atmosphere, dried 4 hr at 120° C., and calcined 2 hr at 400° C. then 12 hr at 530° C. in an air stream, and the 16–28 mesh fractions were collected to produce H-ZSM-5/Al$_2$O$_3$.

The H-ZSM-5/Al$_2$O$_3$ (15 g) thus obtained was packed in a quartz reaction tube, and phenol was ethylated with ethylene by a fixed-bed flow system. Incidentally, water was added as a promoter of this reaction. The reaction was performed at 400° C. under atmospheric pressure with molar ratio of phenol/ethylene/water = 1.0/0.8/1.3, and with WHSV = 12 hr$^{-1}$. Analysis of the liquid reaction product by gas chromatography gave the results shown in Table 1.

TABLE 1

Composition of Liquid Products Produced
with H-ZSM-5/Al$_2$O$_3$ Catalyst

| Compound Name | Wt % |
|---|---|
| Light hydrocarbons | 1.6 |
| Phenol | 49.8 |
| o-Ethylphenol | 11.7 |
| m-Ethylphenol | 20.0 |
| p-Ethylphenol | 6.6 |
| Diethylphenol etc. | 10.3 |
| $\frac{\text{m-Ethylphenol}}{\text{m-Ethylphenol + p-Ethylphenol}} \times 100$ | 75.2 |

The liquid product was then distilled under a reduced pressure with an Oldershow distillation column with 25 plates, and the m- and p-ethylphenol fraction was collected to give an ethylphenol mixture containing m- and p-ethylphenols. The composition of this mixture is shown in Table 2.

TABLE 2

Composition of m- and p-Ethylphenol Fraction

| Compound Name | Wt % |
|---|---|
| o-Ethylphenol | 0.1 |
| m-Ethylphenol | 74.9 |
| p-Ethylphenol | 24.8 |
| Diethylphenol etc. | 0.2 |
| $\frac{\text{m-Ethylphenol}}{\text{m-Ethylphenol + p-Ethylphenol}} \times 100$ | 75.1 |

Example 2

This Example illustrates the production of an ethylphenol mixture of m- and p-ethylphenols for use as the raw material of the process of this invention. Accordingly, this Example is not within the scope of this invention, and is given for reference purposes only.

The H-ZSM-5/Al$_2$O$_3$ (15 g) prepared in Example 1 was packed in a quartz reaction tube, and phenol was ethylated with ethanol by a fixed-bed flow system. The reaction was performed at 400° C. under atmospheric pressure with molar ratio of phenol/ethanol=1.0/0.8, and with WHSV=15 hr$^{-1}$. Analysis of the liquid reaction product by gas chromatography gave the results shown in Table 3.

TABLE 3

Composition of Liquid Products Produced
with H-ZSM-5/Al$_2$O$_3$ Catalyst

| Compound Name | Wt % |
|---|---|
| Light hydrocarbons | 1.4 |
| Phenol | 52.0 |
| o-Ethylphenol | 11.4 |
| m-Ethylphenol | 18.8 |
| p-Ethylphenol | 6.5 |
| Diethylphenol etc. | 9.9 |
| $\frac{\text{m-Ethylphenol}}{\text{m-Ethylphenol + p-Ethylphenol}} \times 100$ | 74.3 |

Example 3

This Example illustrates the production of P-ZSM-5/Al$_2$O$_3$ which is not only useful to conduct the process of this invention but also useful for the production of Mg-P-ZSM-5/Al$_2$O$_3$, Ba-P-ZSM-5/Al$_2$O$_3$ and the like used in the following Examples.

The H-ZSM-5/Al$_2$O$_3$ (100 g) prepared in Example 1 was placed in a solution of 11.0 g of diammonium hydrogenphosphate [(NH$_4$)$_2$HPO$_4$] in 400 g of water, and the mixture was allowed to stand at 90° C. for 24 hr. The catalyst was collected by filtration, dried 3 hr at 120° C., then calcined 12 hr at 530° C. in the air to give P-ZSM-5/Al$_2$O$_3$. The phosphorus content as detemined by X-ray fluorescence analysis was 1.1 wt%.

Example 4

The P-ZSM-5/Al$_2$O$_3$ (10 g) prepared in Example 3 was added to a solution of 3.0 g of magnesium acetate [Mg(CH$_3$COO)$_2$·4H$_2$O] in 25 g of water, and was allowed to stand for 24 hr at 90° C. The catalyst was collected by filtration, dried 3 hr at 120° C., then calcined 12 hr at 530° C. in the air to give Mg-P-ZSM-5/Al$_2$O$_3$. The magnesium and phosphorus contents as determined by X-ray fluorescence analysis were 1.8 and 1.1 wt% respectively.

This Mg-P-ZSM-5/Al$_2$O$_3$ (5 g) was packed in a quartz fixed-bed flow reactor, and the ethylphenol mixture containing m- and p-ethylphenols obtained in Example 1 (Table 4; raw material) was charged as the raw material together with water (raw material/water weight ratio=1/1) at a reaction temperature of 450° C. and with WHSV=8 hr$^{-1}$. The products were separated into gaseous and liquid products, the quantities of each product was measured and compositions were determined by gas chromatography. The total product composition was calculated from the quantities and compositions of the gaseous and liquid products. The compositions of the reaction products are shown in Table 4. The liquid product thus obtained was distilled with an Oldershow type distillation column with 25 plates, and the m-and p-ethylphenol fraction was collected to give m-ethylphenol with a purity of 98.6 wt%. The impurities were mainly of p-ethylphenol.

Example 5

The P-ZSM-5/Al$_2$O$_3$ (10 g) prepared in Example 3 was added to a solution of 3.0 g of barium acetate [Ba(CH$_3$COO)$_2$] in 25 g of water, and was treated similarly as described in Example 4 to give Ba-P-ZSM-5/Al$_2$O$_3$. The barium and phosphorus contents as determined by X-ray fluorescence analysis were 7.9 and 1.1 wt% respectively.

This Ba-P-ZSM-5/Al$_2$O$_3$ catalyst (5 g) was packed in a quartz fixed-bed flow reactor, and the ethylphenol mixture containing m- and p-ethylphenols was allowed to react by the procedure exactly identical to Example 4. The compositions of the reaction products thus obtained are shown in Table 4.

Example 6

The P-ZSM-5/Al$_2$O$_3$ (10 g) prepared in Example 3 was added to a solution of 5.0 g of manganese acetate [Mn(CH$_3$COO)$_2$·4H$_2$O] in 25 g of water, and was treated similarly as described in Example 4 to give Mn-P-ZSM-5/Al$_2$O$_3$. The manganese and phosphorus contents were 4.0 and 1.1 wt% respectively.

This Mn-P-ZSM-5/Al$_2$O$_3$ catalyst (5 g) was packed in a quartz fixed-bed flow reactor, and the ethylphenol mixture containing m- and p-ethylphenols was allowed to react by the procedure exactly identical to Example 4. The compositions of the reaction products thus obtained are shown in Table 4.

Example 7

The P-ZSM-5/Al$_2$O$_3$ (10 g) prepared in Example 3 was added to a solution of 5.0 g of cobalt acetate [Co(CH$_3$COO)$_2$·4H$_2$O] in 25 g of water, and was treated similarly as described in Example 4 to give Co-P-ZSM-5/Al$_2$O$_3$. The cobalt and phosphorus contents were 4.6 and 1.1 wt% respectively.

This Co-P-ZSM-5/Al$_2$O$_3$ catalyst (5 g) was packed in a quartz fixed-bed flow reactor, and the ehtylphenol mixture containing m- and p-ethylphenols was allowed to react by the procedure exactly identical to Example 4. The compositions of the reaction products thus obtained are shown in Table 4.

Example 8

The H-ZSM-5/Al$_2$O$_3$ (10 g) prepared in Example 1 was placed in a flask and a mixture of 10 g of tetramethoxysilane in 250 g of toluene was added, and the mixture was refluxed for 5 hr at 90° C. The mixture was filtered and the solids were dried at an ambient atmosphere and calcined 2 hr at 200° C. then 12 hr at 530° C. in an air stream to give Si-ZSM-5/Al$_2$O$_3$. The silicon content as determined by X-ray fluorescence analysis was 2.4 wt%.

This Si-ZSM-5/Al$_2$O$_3$ catalyst (5 g) was packed in a quartz fixed-bed flow reactor; and the ethylphenol mixture containing m- and p-ethylphenols was allowed to react by the procedure exactly identical to Example 4. The compositions of the reaction products thus obtained are shown in Table 4.

Example 9

The P-ZSM-5/Al$_2$O$_3$ (10 g) prepared in Example 3 was added to a solution of 3.0 g of strontium nitrate [Sr(NO$_3$)$_2$·4H$_2$O] in 25 g of water, and was treated similarly as described in Example 4 to give Sr-P-ZSM-5/Al$_2$O$_3$. The strontium and phosphorus contents were 3.7 and 1.1 wt% respectively.

This Sr-P-ZSM-5/Al$_2$O$_3$ catalyst (5 g) was packed in a quartz fixed-bed flow reactor, and the ethylphenol mixture containing m- and p-ethylphenols was allowed to react by the procedure exaclty identical to Example 4. The compositions of the reaction products thus obtained are shown in Table 4.

Example 10

The P-ZSM-5/Al$_2$O$_3$ (10 g) prepared in Example 3 was added to a solution of 4.0 g of calcium acetate [Ca(CH$_3$COO)$_2$·H$_2$O] in 25 g of water, and was treated similarly as described in Example 4 to give Ca-P-ZSM-5/Al$_2$O$_3$. The calcium and phosphorus contents were 3.1 and 1.1 wt%, respectively.

This Ca-P-ZSM-5/Al$_2$O$_3$ catalyst (5 g) was packed in a quartz fixed-bed flow reactor, and the ethylphenol mixture containing m- and p-ethylphenols was allowed to react by the procedure exactly identical to Example 4. The compositions of the reaction products thus obtained are shown in Table 4.

Example 11

The H-ZSM-5/Al$_2$O$_3$ (100 g) prepared by the same procedure as used in Example 1 was placed in a solution of 17.6 g of diammonium hydrogenphosphate [(NH$_4$)$_2$HPO$_4$] in 400 g of water, and the mixture was allowed to stand at 90° C. for 24 hr. The catalyst was collected by filtration, dried 3 hr at 120° C., then calcined 12 hr at 530° C. in the air to give P-ZSM-5/Al$_2$O$_3$. The phosphorus content as determined by X-ray fluorescence analysis was 1.8 wt%.

This P-ZSM-5/Al$_2$O$_3$ catalyst (5 g) was packed in a quartz fixed-bed flow reactor, and the ethylphenol mixture containing m- and p-ethylphenols was allowed to react by the procedure exactly identical to Example 4. The compositions of the reaction products thus obtained are shown in Table 4.

Example 12

Na-ZSM-11 with a silica/alumina molar ratio of 70 was prepared according to U.S. Pat. No. 3,709,979. The Na-ZSM-11 thus obtained had a silica/alumina molar ratio of 65 as determined by X-ray fluorescence analysis, and had an average crystalline diameter of 0.5 μm as determined by electron microscope. This Na-ZSM-11 (60 g) was soaked in 1,000 ml of 1N aqueous ammonium nitrate, heated for 24 hr at 80° C. and kept as it stands, and then the supernatant solution was removed by decantation. The addition of 1,000 ml of 1N aqueous ammonium nitrate, heating, and decantation described above were repeated three more times, and the solid was washed with water and dried overnight at 120° C. to produce NH$_4$-ZSM-11.

This NH$_4$-ZSM-11 was calcined 10 hr at 530° C. in an air stream, and then the calcined material was crushed by a press and the 16–28 mesh fractions were collected to produce H-ZSM-11.

The H-ZSM-11 thus obtained (10 g) was placed in a flask and a solution of 10 g of tetramethoxysilane in 250 g of toluene was added, and the mixture was heated for 24 hr at 90° C. Then the solution was filtered and the cakes were dried in an air stream.

The tetramethoxysilane content of the catalyst thus obtained was measured by X-ray fluorescence analysis, and found that the silicon content was 3 wt%. This H-ZSM-11 catalyst (5 g) was packed in a quartz fixed-bed flow reactor, and the ethylphenol mixture containing m- and p-ethylphenols obtained in Example 1 together with water (raw material/water weight ratio=1/1) were charged continuously to the reactor, and reacted at a reaction temperature of 480° C. and with WHSV=6 hr$^{-1}$. The compositions of the reaction products thus obtained are shown in Table 4.

Example 13

This Example is given for comparison purpose and is not within the scope of this invention.

The H-ZSM-5/Al$_2$O$_3$ (5 g) prepared in Example 1 was packed in a quartz fixed-bed flow reactor, and the ethylphenol mixture containing m- and p-ethylphenols was allowed to react by the procedure exactly identical to Example 4. The compositions of the reaction products thus obtained are shown in Table 4.

The value:

$$\frac{\text{m-ethylphenol}}{\text{m-ethylphenol + p-ethylphenol}} \times 100$$

of the product was 75.0% which is almost identical with the value of the raw material, and the recovery yield of m-ethylphenol was as low as 7.6%.

TABLE 4

| | Raw Material | Ex. 4 | Ex. 5 | Ex. 6 | Ex. 7 | Ex. 8 | Ex. 9 | Ex. 10 | Ex. 11 | Ex. 12 | Ex. 13 |
|---|---|---|---|---|---|---|---|---|---|---|---|
| Products composition (wt %) | | | | | | | | | | | |
| Ethylene | 0 | 7.1 | 7.8 | 7.3 | 7.1 | 7.0 | 7.6 | 7.5 | 8.7 | 7.9 | 19.6 |
| Phenol | 0 | 24.0 | 26.2 | 24.6 | 23.7 | 23.5 | 25.5 | 25.1 | 29.4 | 26.5 | 67.0 |
| o-Ethylphenol | 0.1 | 0.1 | 0.1 | 0.1 | 0.1 | 0.1 | 0.1 | 0.1 | 0.1 | 0.1 | 3.4 |
| m-Ethylphenol | 74.9 | 67.7 | 63.1 | 66.7 | 65.5 | 68.2 | 64.1 | 65.1 | 58.4 | 61.4 | 5.7 |
| p-Ethylphenol | 24.8 | 0.9 | 2.6 | 1.1 | 3.4 | 1.0 | 2.5 | 2.0 | 3.1 | 3.9 | 1.9 |
| Diethylphenol etc. | 0.2 | 0.2 | 0.2 | 0.2 | 0.2 | 0.2 | 0.2 | 0.2 | 0.3 | 0.2 | 2.4 |
| $\dfrac{\text{m-EP}^{*1}}{\text{m-EP} + \text{p-EP}^{*2}} \times 100$ | 75.1 | 98.7 | 96.0 | 98.4 | 95.1 | 98.6 | 96.2 | 97.0 | 95.0 | 94.0 | 75.0 |
| Decomposition rate of p-ethylphenol[*3] (%) | — | 96.4 | 89.5 | 95.6 | 86.3 | 96.0 | 89.9 | 91.9 | 87.5 | 84.2 | 92.3 |
| Recovery yield of m-ethylphenol[*4] (%) | — | 90.4 | 84.2 | 89.0 | 87.4 | 91.1 | 85.5 | 86.9 | 78.0 | 82.0 | 7.6 |

[*1] m-EP means m-ethylphenol.
[*2] p-EP means p-ethylphenol.
[*3] Calculated by the next formula:
$$\frac{\text{p-EP(wt \%) in the raw material} - \text{p-EP(wt \%) in the product}}{\text{p-EP(wt \%) in the raw material}} \times 100$$
[*4] Calculated by the next formula:
$$\frac{\text{m-EP(wt \%) in the product}}{\text{m-EP(wt \%) in the raw material}} \times 100$$

We claim:

1. A process for the recovery of high-purity m-ethylphenol characterized in that p-ethylphenol is selectively dealkylated by allowing to contact a mixture of ethylphenols containing m- and p-ethylphenols under heating with (i) a crystalline aluminosilicate catalyst which is obtained by calcining a crystalline aluminosilicate with a constraint index of 1–15, after it is incorporated with one or more compounds containing phosphorus and one or more compounds containing the element selected from the group consisting of manganese, cobalt, silicon and the Group IIA elements of the Periodic Table, or incorporated with one or more compounds containing silicon or phosphorus, or (ii) a crystalline aluminosilicate catalyst which is obtained by incorporating one or more compounds containing silicon to a crystalline aluminosilicate with a constraint index of 1–15, without subjecting to calcination.

2. The process of claim 1, wherein said catalyst is a catalyst of said group (i).

3. The process of claim 2, wherein said catalyst is a crystalline aluminosilicate catalyst which is obtained by calcining a crystalline aluminosilicate with a constraint index of 1–15, after it is incorporated with one or more compounds containing phosphorus and one or more compounds containing the element selected from the group consisting of manganese, cobalt, and the Group IIA elements of the Periodic Table, or incorporated with one or more compounds containing silicon or phosphorus.

4. The process of claim 1, wherein said catalyst is a catalyst of said group (ii).

5. The process of claim 1, wherein said crystalline aluminosilicate is a zeolite having a silica/alumina molar ratio of not less than 20.

6. The process of claim 5, wherein said zeolite is selected from the group consisting of ZSM-5, ZSM-11, ZSM-12, ZSM-35 and ZSM-38.

7. The process of claim 6, wherein said zeolite is a pentasil-type zeolite of ZSM-5 or ZSM-11.

8. The process of claim 1, wherein said Group IIA element is selected from the group consisting of magnesium, calcium, strontium and barium.

9. The process of claim 8, wherein said compound containing Group IIA element of Periodic Table is selected from the group consisting of carboxylates, carbonates, sulfates, nitrate and halides.

10. The process of claim 1, wherein said compound containing phosphorus is selected from the group consisting of ammonium phosphate, diammonium hydrogenphosphate, ammonium dihydrogenphosphate, diphenylphosphine chloride, trimethyl phosphite, phosphorus trichloride, phosphoric acid, phenylphosphonic dichloride, trimethyl phosphate, diphenyl phosphite, diphenylphosphinic acid, acidic methyl phosphate and other acidic esters of phosphoric acid.

11. The process of claim 1, wherein said compound containing manganese or cobalt is selected from the group consisting of carboxylates, carbonate, sulfates, nitrates and halides.

12. The process of claim 1, wherein said compound containing silicon is selected from the group consisting of silanes and silicone compounds.

13. The process of claim 1, wherein the content of phosphorus, manganese, cobalt, silicon or Group IIA element of Periodic Table calculated as element incorporated in said crystalline aluminosilicate is 0.2–40 wt% based on said crystalline aluminosilicate.

14. The process of claim 1, wherein said ethylphenol mixture containing m- and p-ethylphenols is an ethylphenol mixture containing m- and p-ethylphenols as the major components obtained by ethylation of phenol.

15. The process of claim 14, wherein said ethylphenol mixture containing m- and p-ethylphenols as the major components has a molar ratio of m-ethylphenol/p-ethylphenol of from 0.5 to 20.

16. The process of claim 1, wherein said heating is conducted at a temperature of 350°–550° C.

17. The process of claim 1, wherein said mixture is contacted with said catalyst in a weight hourly space velocity of 0.05–100 hr$^{-1}$.

18. The process of claim 1, wherein said mixture is contacted with said catalyst under a pressure of lower than 50 Kg/cm$^2$.

19. The process of claim 1, wherein said mixture is contacted with said catalyst in a vapor phase.

20. The process of claim 2, wherein said crystalline aluminosilicate is a zeolite having a silica/alumina molar ratio of not less than 20; the content of phosphorus, manganese, cobalt, silicon or Group IIA element of Periodic Table calculated as element incorporated in said crystalline aluminosilicate is 0.2–40 wt% based on said crystalline aluminosilicate; said ethylphenol mixture containing m- and p-ethylphenols is an ethylphenol mixture containing m- and p-ethylphenols as the major components obtained by ethylation of phenol; and dealkylation reaction is conducted in a vapor phase at a temperature of 350°–550° C. in a weight hourly space velocity of 0.05–100 hr$^{-1}$ under a pressure of lower than 50 Kg/cm$^2$.

21. The process of claim 20, wherein said compound containing Group IIA element of Periodic Table is selected from the group consisting of carboxylates, carbonates, sulfates, nitrates and halides.

22. The process of claim 20, wherein said compound containing phosphorus is selected from the group consisting of ammonium phosphate, diammonium hydrogenphosphate, ammonium dihydrogenphosphate, diphenylphosphine chloride, trimethyl phosphite, phosphorus trichloride, phosphoric acid, phenylphosphonic dichloride, trimethyl phosphate, diphenyl phosphite, diphenylphosphinic acid, acidic methyl phosphate and other acidic esters of phosphoric acid.

23. The process of claim 20, wherein said compound containing manganese or cobalt is selected from the group consisting of carboxylates, carbonates, sulfates, nitrates and halides.

24. The process of claim 20, wherein said compound containing silicon is selected from the group consisting of silanes and silicone compounds.

* * * * *